(12) United States Patent
Choi et al.

(10) Patent No.: US 12,090,221 B2
(45) Date of Patent: Sep. 17, 2024

(54) COMPOSITION FOR PREVENTING GRAY HAIR, PROMOTING BLACK HAIR AND PREVENTING, IMPROVING OR TREATING VITILIGO OR HYPOCHROMATISM COMPRISING FRUCTOSE 1,6-BISPHOSPHATE OR SALT, SOLVATE, STEREOISOMER OR HYDRATE THEREOF AS ACTIVE INGREDIENT

(71) Applicant: AMOREPACIFIC CORPORATION, Seoul (KR)

(72) Inventors: Hyunjung Choi, Yongin-si (KR); Seunghyun Shin, Yongin-si (KR); Hyoung June Kim, Yongin-si (KR); Wonseok Park, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 127 days.

(21) Appl. No.: 17/578,949

(22) Filed: Jan. 19, 2022

(65) Prior Publication Data
US 2022/0226220 A1    Jul. 21, 2022

(30) Foreign Application Priority Data

Jan. 19, 2021   (KR) .................. 10-2021-0007529
May 20, 2021   (KR) .................. 10-2021-0064571

(51) Int. Cl.
| | |
|---|---|
| *A61K 8/55* | (2006.01) |
| *A61K 8/60* | (2006.01) |
| *A61K 31/7024* | (2006.01) |
| *A61P 7/00* | (2006.01) |
| *A61P 17/00* | (2006.01) |
| *A61Q 5/10* | (2006.01) |

(52) U.S. Cl.
CPC .............. *A61K 8/556* (2013.01); *A61K 8/60* (2013.01); *A61K 31/7024* (2013.01); *A61P 17/00* (2018.01); *A61Q 5/10* (2013.01)

(58) Field of Classification Search
CPC ...... A61K 8/556; A61K 8/60; A61K 31/7024; A61P 17/00; A61Q 5/10
See application file for complete search history.

(56) References Cited

U.S. PATENT DOCUMENTS

| | | | |
|---|---|---|---|
| 6,051,244 A | * | 4/2000 | Perricone ............... A61Q 19/00 514/23 |
| 2004/0180100 A1 | | 9/2004 | Fung et al. |
| 2005/0175556 A1 | | 8/2005 | Gupta |

FOREIGN PATENT DOCUMENTS

| | | | |
|---|---|---|---|
| CN | 1209052 A | | 2/1999 |
| KR | 20030087680 A | * | 11/2003 |
| KR | 20030090367 A | * | 11/2003 |
| KR | 10-2003-0092204 A | | 12/2003 |
| KR | 20030092204 A | * | 12/2003 |
| KR | 10-2009-0076536 A | | 7/2009 |
| KR | 10-2012-0023934 A | | 3/2012 |
| KR | 10-2015-0043268 A | | 4/2015 |
| WO | 97/24105 A1 | | 7/1997 |

OTHER PUBLICATIONS

Jiaxiang Sun et al., "Fructose 1-6 Diphosphate Prevents Intestinal Ischemic Reperfusion Injury and Death in Rats", Gastroenterology, 1990, vol. 98, pp. 117-126.
Lynn Edde et al., "Induction of Nitric Oxide Synthase in Macrophages: Inhibition by Fructose-1,6-diphosphate", Biochemical and Biophysical Research Communications, 1998, vol. 243, pp. 683-687.
Soo Mi Ahn et al., "Fructose 1,6-diphosphate Prevents Cyclooxygenase-2 and Matrix Metalloproteinases Expression by Inhibition of UVB-induced Signaling Cascades in HaCaT Keratinocytes", J. Soc. Cosmet. Scientists Korea, 2004, vol. 30, No. 2, pp. 247-251.

* cited by examiner

*Primary Examiner* — Abigail Vanhorn
(74) *Attorney, Agent, or Firm* — Merchant & Gould P.C.

(57) ABSTRACT

The present disclosure relates to a composition for preventing gray hair, promoting black hair and preventing, improving or treating vitiligo or hypochromatism, which contains fructose 1,6-bisphosphate or a salt, a solvate, a stereoisomer or a hydrate thereof as an active ingredient, and has been contrived to solve the problem of the prior art that appreciable effect cannot be achieved due to insignificant effect on melanin production. The composition of the present disclosure, which contains fructose 1,6-bisphosphate or a salt, a solvate, a stereoisomer or a hydrate thereof, provides superior effect of preventing gray hair, promoting black hair and treating vitiligo or hypochromatism.

11 Claims, 2 Drawing Sheets

[FIG. 1]
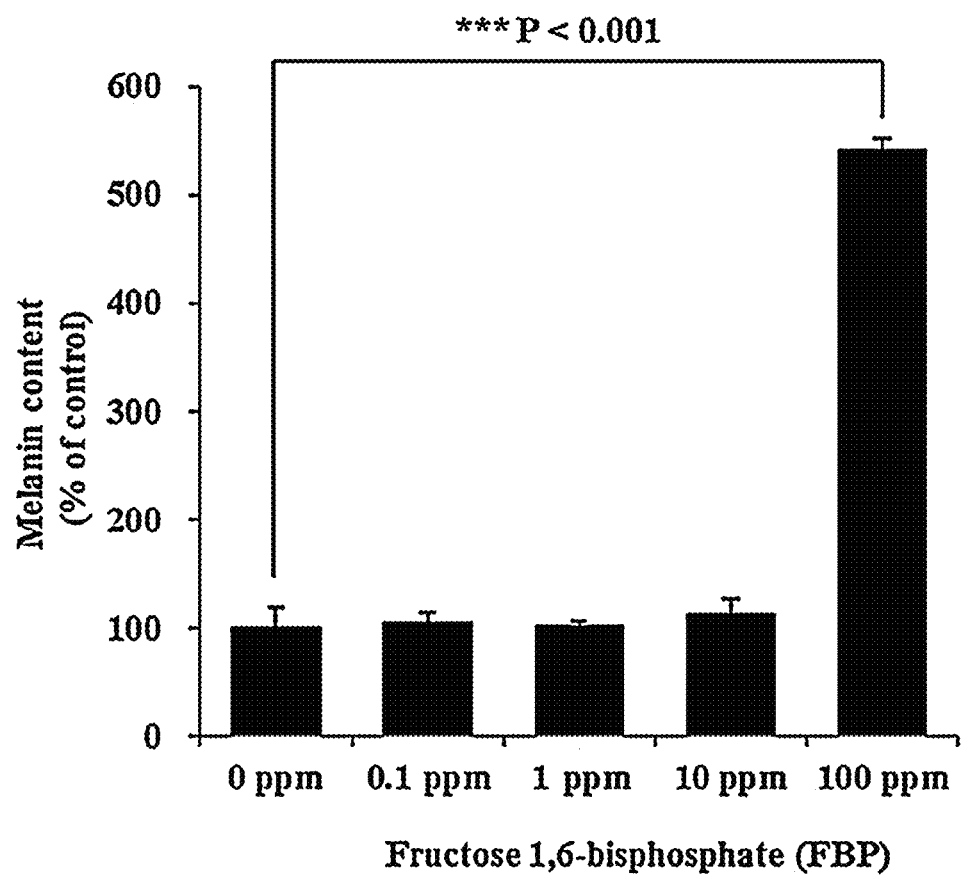

[FIG. 2]
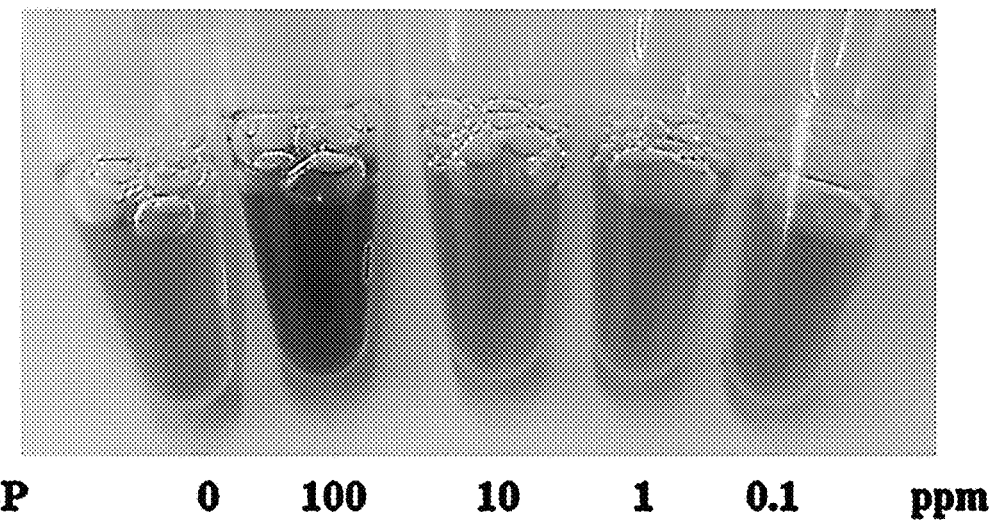
FBP    0    100    10    1    0.1    ppm
[FIG. 3]
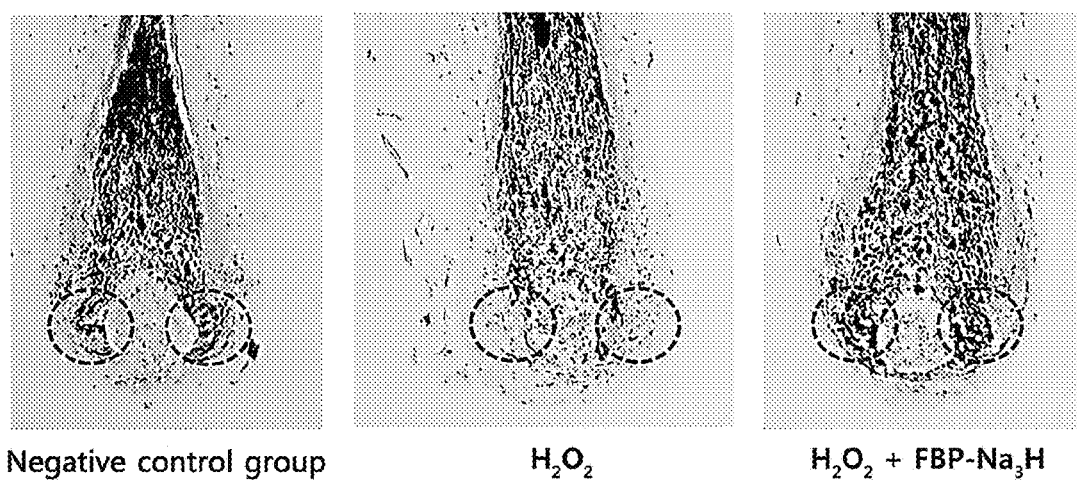
Negative control group     $H_2O_2$     $H_2O_2$ + FBP-$Na_3$H

COMPOSITION FOR PREVENTING GRAY HAIR, PROMOTING BLACK HAIR AND PREVENTING, IMPROVING OR TREATING VITILIGO OR HYPOCHROMATISM COMPRISING FRUCTOSE 1,6-BISPHOSPHATE OR SALT, SOLVATE, STEREOISOMER OR HYDRATE THEREOF AS ACTIVE INGREDIENT

CROSS-REFERENCE TO RELATED APPLICATION

This application claims the priorities of Korean Patent Application No. 10-2021-0007529 filed on Jan. 19, 2021, Korean Patent Application No. 10-2021-0064571 filed on May 20, 2021, and all the benefits accruing therefrom under 35 U.S.C. §119, the contents of which in their entirety are herein incorporated by reference.

TECHNICAL FIELD

Disclosed in the present specification is a composition for preventing gray hair, promoting black hair and preventing, improving or treating vitiligo or hypochromatism, which contains fructose 1,6-bisphosphate or a salt, a solvate, a stereoisomer or a hydrate thereof as an active ingredient.

BACKGROUND ART

Hair graying refers to the process wherein hair such as head hair, eyebrows, eyelashes, etc. turns light gray or white. It is known that hair graying is caused by the decreased number of melanocytes that produce the pigment melanin in hair follicles deficiency of the pigment due to decreased transport of melanin to nearby keratinocytes. The pigmentation of head hair and bodily hair requires the presence of melanocytes in the hair bulb of the hair follicle. The melanin produced in melanocytes is transmitted to keratinocytes for formation of the hair stalk that will result in the growth of pigmented strands of head hair or bodily hair. This structure is known as a "follicular pigmentation unit". Thus, the normal cycle of the melanocytes in the human hair follicle requires the presence of melanocyte precursors in the upper region of the hair follicle, which will be periodically activated to regenerate the follicular pigmentation unit.

Vitiligo is an acquired depigmenting disorder caused by the loss of melanocytes, characterized by depigmented patches of various sizes and shapes on skin. Globally, 1-2% of people are affected by vitiligo. The patient may suffer from severe problems in terms of beauty care and interpersonal relationships.

Hypochromatism is a disease histologically vitiligo, which is characterized by lesions with almost nonexistent melanin. Whereas the pigment is destroyed on its own in vitiligo, hypochromatism is caused by skin diseases such as atopic dermatitis, inflammatory dermatitis, etc.

Korean Patent Publication No. 10-2009-0076536 discloses an essential oil for treating vitiligo and gray hair, which has been extracted from lotus. However, the essential oil does not exhibit appreciable effect due to insignificant effect on melanin production. Accordingly, further research and development are necessary on a superior composition for preventing gray hair, promoting black hair and treating vitiligo or hypochromatism.

DISCLOSURE

[Technical Problem]

The inventors of the present disclosure have researched for a substance which is useful for preventing gray hair, promoting black hair and preventing, improving or treating vitiligo or hypochromatism, and have completed the present disclosure by finding out the superior effect of fructose 1,6-bisphosphate or a salt, a solvate, a stereoisomer or a hydrate thereof. Therefore, the present disclosure is directed to providing a composition for preventing gray hair, promoting black hair and preventing, improving or treating vitiligo or hypochromatism.

[Technical Solution]

The present disclosure provides a composition for preventing gray hair, promoting black hair and preventing, improving or treating vitiligo or hypochromatism, which contains fructose 1,6-bisphosphate or a salt, a solvate, a stereoisomer or a hydrate thereof as an active ingredient.

[Advantageous Effects]

A composition of the present disclosure, which contains fructose 1,6-bisphosphate or a salt, a solvate, a stereoisomer or a hydrate thereof, provides superior effect of preventing gray hair, promoting black hair and treating vitiligo or hypochromatism.

BRIEF DESCRIPTION OF DRAWINGS

FIG. 1 shows the effect of fructose 1,6-bisphosphate on promotion of melanin synthesis in normal human melanocytes depending on concentration.

FIG. 2 shows the effect of fructose 1,6-bisphosphate on promotion of melanin synthesis in normal human melanocytes depending on concentration.

FIG. 3 shows the effect of a fructose 1,6-bisphosphate trisodium salt on prevention of gray hair and promotion of black hair in human hair follicles.

BEST MODE

The terms used in the present specification were selected from currently widely general terms in consideration of the function in the present disclosure. However, they may vary depending on the intent of those skilled in the art, precedents, emergence of new technologies, etc. In addition, there may be terms that are arbitrarily selected by the applicant. In that case, their meaning will be described clearly in the corresponding part in the description of the present disclosure. Accordingly, the terms used in the present disclosure should be interpreted based on the contexts throughout the present disclosure, not simply the name of the terms.

Unless defined otherwise, all the terms used herein including technological or scientific terms have the same meaning as those commonly understood by those having ordinary knowledge in the art to which the present disclosure belongs. The terms should be interpreted as the same meanings as the contextual meanings of a related technology, and should not be interpreted as ideal or excessively formal meanings unless defined clearly otherwise in the present disclosure.

Numerical ranges include the numerical values defined in the present disclosure. All maximum numerical limitation recited in the present specification is intended to include all lower numerical limitations. Any minimum numerical limitation recited in the present specification is intended to include all higher numerical limitations. All numerical limitations given throughout the present specification will include all better numerical ranges within a narrower range.

As used herein, the words "comprising", "having", "containing (or including)" are inclusive or open-ended and do not exclude additional, unmentioned elements or steps. The term "or a combination thereof" used herein refers to all permutations and combinations of the items listed above. For example, "A, B, C or a combination thereof" is intended to include at least one of A, B, C, AB, AC, BC or ABC and, if order is important in a particular context, also BA, CA, CB, CBA, BCA, ACB, BAC or CAB. In addition, combinations including repeats of one or more item, e.g., BB, AAA, MB, BBC, AAABCCCC, CBBAAA, CABABB, etc., are included expressly. Those having ordinary skill will understand that there is no limit on the number of items in any combination unless apparent otherwise from the context.

Hereinafter, exemplary embodiments of the present disclosure will be described in detail referring to the attached drawings. However, it is obvious that the present disclosure is not limited by the exemplary embodiments or drawings.

In an aspect, the present disclosure provides a composition for preventing gray hair or promoting black hair, which contains fructose 1,6-bisphosphate or a salt, a solvate, a stereoisomer or a hydrate thereof as an active ingredient. In an aspect, the present disclosure provides a composition for preventing, improving or treating vitiligo or hypochromatism, which contains fructose 1,6-bisphosphate or a salt, a solvate, a stereoisomer or a hydrate thereof as an active ingredient. In an aspect, the present disclosure provides a composition for promoting melanin production, which contains fructose 1,6-bisphosphate or a salt, a solvate, a stereoisomer or a hydrate thereof as an active ingredient.

The fructose 1,6-bisphosphate (FBP) is an intermediate produced during glycolysis. It is known to have the effect of protecting cells from tissue damage caused by reperfusion following hypoxia or ischemia in the heart or brain [*Gastroenterology*, (1990) 98: 117-126]. In addition, it is reported to inhibit the production of nitric oxide caused by endotoxin rat macrophages [*Biochemical and Biophysical Research Communication*, (1998) 243:683-687]. Although the mechanism action of fructose 1,6-bisphosphate in the cells is not known accurately yet, fructose 1,6-bisphosphate is an important substance which regulates various reactions occurring in cells and is involved in metabolic processes.

The fructose 1,6-bisphosphate of the present disclosure may be commonly available fructose 1,6-bisphosphate. Not only pure fructose 1,6-bisphosphate but also derivatives of fructose 1,6-bisphosphate may be used. The derivatives may be in the form of salts. The salts may be cosmetically, sitologically and/or pharmaceutically acceptable salts, and may be specifically acid addition salts formed from free acids. The acid addition salt may be an inorganic acid such as hydrochloric acid, nitric acid, phosphoric acid, sulfuric acid, hydrobromic acid, hydroiodic acid, nitrous acid, phosphorous acid, etc., a non-toxic organic acid such as aliphatic mono- and dicarboxylate, phenyl-substituted alkanoate, hydroxyalkanoate and alkanedioate, aromatic acids, aliphatic and aromatic sulfonates, or an organic acid such as trifluoroacetic acid, acetate, benzoic acid, citric acid, lactic acid, maleic acid, gluconic acid, methanesulfonic acid, 4-toluenesulfonic acid, tartaric acid, fumaric acid, etc. The acid addition salt may be prepared by a common method, for example, by dissolving the compound in an organic solvent such as methanol, ethanol, acetone, methylene chloride, acetonitrile, etc., adding an organic acid or an inorganic acid, and then filtering and drying the produced precipitate, or distilling the solvent and excess acid under reduced pressure, drying and then crystallizing the product in an organic solvent.

Examples of cosmetically, sitologically and/or pharmaceutically non-toxic salts include sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, manolnate, succinate, suberate, sebacate, fumarate, maleate, butene-1,4-dioate, hexane-1,6-dioate, benzoate, chlorobenzoate, methyl benzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate, mandelate, etc.

In addition, the salt may be a metal salt prepared using a base. An alkali metal or alkaline earth metal salt is obtained by, for example, dissolving the compound in a solution of excess alkali metal hydroxide or alkaline earth metal hydroxide, filtering the undissolved salt of the compound, and evaporating and drying the filtrate. The metal salt may be a barium salt, a dibarium salt, a sodium salt, a disodium salt, a tetrasodium salt, a potassium salt, a calcium salt, a dicalcium salt, a dimagnesium salt or a tricyclohexylamine salt. In addition, the alkali metal or alkaline earth metal salt may be reacted with a suitable silver salt (e.g., zinc nitrate) to obtain corresponding salts.

In addition, the composition of the present disclosure may contain, not only the salt of fructose 1,6-bisphosphate as a derivative, but also a solvate, stereoisomer, hydrate, etc. that may be prepared therefrom.

The "solvate" refers to a compound of the present disclosure, which includes a stoichiometric or non-stoichiometric amount of a solvent bound by non-covalent intermolecular forces. Preferred solvents are those which are volatile, non-toxic and and/or acceptable for administration to human.

The term "stereoisomer" refers to a compound that has an identical molecular formula and an identical method of linking constituent atoms, but has different spatial arrangement between atoms. The stereoisomer may be a diastereomer or an enantiomer. A diastereomer refers to a stereoisomer which does not a mirror image relationship, and may be divided into cis-trans isomers depending on the spatial arrangement of atoms. The enantiomer refers to an isomer which is one of two stereoisomers that are non-superimposable, much as one's left and right hands are mirror images of each other, and is also called an optical isomer. The enantiomer is divided into R (rectus: clockwise) and S (sinister: counterclockwise) when four different substituents are attached to a chiral carbon atom. These isomers and their mixtures are also included in the present disclosure.

The term "hydrate" refers to a compound which includes a stoichiometric or non-stoichiometric amount of water bound by a non-covalent intermolecular force. The hydrate may include 1 or more equivalents, specifically 1-5 equivalents, of water. The hydrate may be prepared by crystallizing the compound of the present disclosure from water or a water-containing solvent.

The "active ingredient" refers to an ingredient which exhibits desired activity by itself or when used together with an inert carrier. The expression "containing (comprising) as an active ingredient" may mean that the ingredient is contained as an ingredient which exhibits the effect of preventing gray hair, improving black hair and/or preventing, improving or treating vitiligo or hypochromatism.

The composition of the present disclosure may be usefully used as a composition for increasing the intracellular level of melanin, preventing gray hair, promoting black hair and preventing, improving or treating vitiligo or hypochromatism.

In an exemplary embodiment of the present disclosure, a daily application dosage of the fructose 1,6-bisphosphate or a salt, a solvate, a stereoisomer or a hydrate thereof may be more than 10 mg/kg and less than 10,000 mg/kg. The daily application dosage may vary depending on the age, sex or body weight of a subject, the particular disease or pathological condition possessed by the subject, the severity of the disease or pathological condition, administration route, etc., and the determination of the application dosage based on these factors is within the level of those skilled in the art. More specifically, the daily application dosage may be more than 10 mg/kg, 11 mg/kg or more, 12 mg/kg or more, 13 mg/kg or more, 14 mg/kg or more, 15 mg/kg or more, 16 mg/kg or more, 17 mg/kg or more, 18 mg/kg or more, 19 mg/kg or more, 20 mg/kg or more, 30 mg/kg or more, 40 mg/kg or more, 50 mg/kg or more, 60 mg/kg or more, 70 mg/kg or more, 80 mg/kg or more, 90 mg/kg or more or 100 mg/kg or more, and less than 10,000 mg/kg, 9,000 mg/kg or less, 8,000 mg/kg or less, 7,000 mg/kg or less, 6,000 mg/kg or less, 5,000 mg/kg or less, 4,000 mg/kg or less, 3,000 mg/kg or less, 2,000 mg/kg or less, 1,000 mg/kg or less, 900 mg/kg or less, 800 mg/kg or less, 700 mg/kg or less, 600 mg/kg or less, 500 mg/kg or less, 400 mg/kg or less, 300 mg/kg or less, 200 mg/kg or less or 100 mg/kg or less, although not being limited thereto. The application may be made once or several times a day.

For example, the application may be made 2-24 times a day, 1-2 times in three days, 1-6 times a week, 1-10 times in two weeks, 1-15 times in three weeks, 1-3 times in four weeks, or 1-12 times a year. The "application" refers to the provision of the composition to a subject by a suitable method including administration, application, absorption, intake, etc. The subject refers to any animal such as human, dog, goat, pig, rat, etc. to which the composition can be applied.

The fructose 1,6-bisphosphate or a salt, a solvate, a stereoisomer or a hydrate thereof may be applied in the form of various formulations for oral or parenteral administration. The formulations are prepared using a commonly used diluent or excipient such as a filler, an extender, a binder, a wetting agent, a disintegrant, a surfactant, etc.

Solid formulations for oral administration include, for example, a tablet, a pill, a powder, a granule, a capsule, etc. These sold formulations are prepared by mixing one or more compound with at least one excipient, e.g., starch, calcium carbonate, sucrose, lactose, gelatin, etc. In addition to a simple excipient, a lubricant such as magnesium stearate, talc, etc. is also used. Liquid formulations for oral administration include, for example, a suspension, a solution for internal use, an emulsion, a syrup, etc. The liquid formulation may contain, in addition to a commonly used simple diluent such as water or liquid paraffin, various excipients, e.g., a wetting agent, a sweetener, an aromatic, a preservative, etc.

Sterilized aqueous solutions for parenteral administration include a nonaqueous solution, a suspension and an emulsion. As a solvent for the nonaqueous solution or suspension, propylene glycol, polyethylene glycol, vegetable oil such as olive oil, injectable ester such as ethyl oleate, etc. may be used. A composition containing the fructose 1,6-bisphosphate or a salt, a solvate, a stereoisomer or a hydrate thereof as an active ingredient may be administered parenterally, and the parenteral administration may be made by subcutaneous, intravenous, intramuscular or intrathoracic injection. For parenteral administration, a solution or a suspension may be prepared by mixing the fructose 1,6-bisphosphate or a salt, a solvate, a stereoisomer or a hydrate thereof in water together with a stabilizer or a buffer, and may be packed into ampoule or vial unit for administration. The composition may be sterilized and/or contain an antiseptic, a stabilizer, a wetting agent, an emulsification accelerator, an adjuvant such as a salt and/or buffer for osmoregulation and other therapeutically useful substances, and may be formulated according to generally known methods such as mixing, granulation or coating.

In an exemplary embodiment of the present disclosure, the content of the fructose 1,6-bisphosphate or a salt, a solvate, a stereoisomer or a hydrate thereof may vary depending on formulation, use, number of application and application route. In particular, when the composition of the present disclosure is prepared into a parenteral formulation such as an injection, etc., or an oral formulation such as a food, a pill, a syrup, etc., the content of the active ingredient in the present disclosure may vary depending on the intestinal absorptivity, digestibility, etc. of the composition. When the composition of the present disclosure is prepared into a formulation for external application to skin and is applied topically, it may be applied with a daily application dosage of more than 60 mg and less than 60,000 mg for a subject with a body weight of 60 kg. Assuming that the daily application dosage is 100 g, the content of the active ingredient of the present disclosure may be less than 0.06-60 wt % based on the total weight of the composition.

In an exemplary embodiment of the present disclosure, the fructose 1,6-bisphosphate or a salt, a solvate, a stereoisomer or a hydrate thereof may be contained in an amount of less than 0.06-60 wt % based on the total weight of the composition. More specifically, it may be contained in an amount of more than 0.06 wt %, 0.07 wt % or more, 0.08 wt % or more, 0.09 wt % or more, 0.1 wt % or more, 0.2 wt % or more, 0.3 wt % or more, 0.4 wt % or more, 0.5 wt % or more or 0.6 wt % or more, and less than 60 wt %, 59 wt % or less, 58 wt% or less, 57 wt % or less, 56 wt % or less, 55 wt % or less, 54 wt% or less, 53 wt % or less, 52 wt % or less, 51 wt % or less, 50 wt % or less, 40 wt % or less, 30 wt % or less, 20 wt % or less, 10 wt % or less, 9 wt % or less, 8 wt % or less, 7 wt % or less, 6 wt % or less, 5 wt % or less, 4 wt % or less, 3 wt % or less, 2 wt % or less, 1 wt % or less, 0.9 wt % or less, 0.8 wt % or less, 0.7 wt % or less or 0.6 wt % or less, although not being limited thereto. Specifically, the fructose 1,6-bisphosphate or a salt, a solvate, a stereoisomer or a hydrate thereof may be contained in an amount of 1-10 wt % based on the total weight of the composition.

In an exemplary embodiment of the present disclosure, the composition promotes the production of melanin in melanocytes. More specifically, the composition promotes differentiation, proliferation and migration by stimulating inactive melanocytes or chromoblasts present in skin or hair follicles and produces melanin. By promoting the production of melanin, the composition of the present disclosure can prevent hair graying in advance and promote hair blackening and can be usefully used as a composition for preventing, improving or treating vitiligo or hypochromatism.

In an exemplary embodiment of the present disclosure, the gray hair is caused by aging. The loss of stem cells of melanocytes, decreased activity of melanocytes and aging are cited as the cause of gray hair. In particular, the gray hair in the present disclosure is caused by aging.

In an exemplary embodiment of the present disclosure, the composition may be a composition for external application to skin. The term "skin" refers to the tissue covering the body surface of an animal. The term is used in the broadest concept, including not only the tissue that covers the surface such as the face, body, etc. but also the scalp and hair.

In an exemplary embodiment of the present disclosure, the composition may be a cosmetic composition. The cosmetic composition may be formulated according to a common method. For formulation, the International Cosmetic Ingredient Dictionary (ICID) published by the Cosmetic, Toiletry and Fragrance Association may be referred to.

Specifically, the composition may be formulated into a hair rinse, a shampoo, a hair conditioner, a hair pack, a hair oil, a hair treatment, a hair cream, a hair lotion, a hair gel, a hair essence, a hair spray, a hair serum, a hair ampoule, a makeup remover, a cleanser, a lotion (softening lotion or nourishing lotion), an emulsion, a cream (nourishing cream or massage cream), a pack, an essence, etc. The formulation may be of rinse-off type or wash-off type, which means that it is removed after being applied to the hair or scalp, or of leave-on type or leave-in type, which means that it remains on the hair or scalp after the application.

The composition may further contain an adjuvant commonly used in the field of cosmetics or dermatology such as a fatty substance, an organic solvent, a solubilizer, a thickener, a gelling agent, a softening agent, an antioxidant, a suspending agent, a stabilizer, a foaming agent, an aromatic, a surfactant, an antiseptic, a pH control agent, water, an ionic or non-ionic emulsifying agent, a filler, a metal ion sequestrant, a chelating agent, a preservative, a blocking agent, a wetting agent, an essential oil, a dye, a pigment, or a hydrophilic or lipophilic activator, depending on the quality or function of the final product.

In an exemplary embodiment of the present disclosure, the composition may be a food composition. The fructose 1,6-bisphosphate or a salt, a solvate, a stereoisomer or a hydrate thereof may be added to a food as it is or together with another food or food ingredient according to a common method. The mixing amount of the active ingredient may be determined adequately depending on the purpose of use (prevention or improvement).

The food composition may be a functional health drink composition, and the drink composition may contain, in addition to the above-described compound, various flavorants or natural carbohydrates as in common beverages. The natural carbohydrate may be, for example, a common sugar such as a monosaccharide, e.g., glucose, fructose, etc., a disaccharide, e.g., maltose, sucrose, etc., a polysaccharide, e.g., dextrin, cyclodextrin, etc. or a sugar alcohol such as xylitol, sorbitol, erythritol, etc. In addition, a natural flavorant (thaumatin, stevia extract (e.g., rebaudioside A, glycyrrhizin, etc.) or a synthetic flavorant (saccharin, aspartame, etc.) may be used.

In an exemplary embodiment of the present disclosure, the composition may be a pharmaceutical composition. The pharmaceutical composition may further contain a pharmaceutical adjuvant such as an antiseptic, a stabilizer, a wetting agent, an emulsification accelerator, a salt and/or buffer for osmoregulation, or other therapeutically useful substances. The pharmaceutical composition may be administered as various formulations for oral or parenteral administration.

In another aspect, the present disclosure provides a use of fructose 1,6-bisphosphate or a salt, a solvate, a stereoisomer or a hydrate thereof for preparation of a composition for preventing gray hair or promoting black hair.

In another aspect, the present disclosure provides a use of fructose 1,6-bisphosphate or a salt, a solvate, a stereoisomer or a hydrate thereof for preparation of a composition for preventing, improving or treating vitiligo or hypochromatism.

In another aspect, the present disclosure provides a use of fructose 1,6-bisphosphate or a salt, a solvate, a stereoisomer or a hydrate thereof for preparation of a composition for promoting melanin production.

In another aspect, the present disclosure provides a method for preventing gray hair or promoting black hair, which includes a step of administering a composition containing fructose 1,6-bisphosphate or a salt, a solvate, a stereoisomer or a hydrate thereof as an active ingredient to a subject in need thereof.

In another aspect, the present disclosure provides a method for preventing, improving or treating vitiligo or hypochromatism, which includes a step of administering a composition containing fructose 1,6-bisphosphate or a salt, a solvate, a stereoisomer or a hydrate thereof as an active ingredient to a subject in need thereof.

In another aspect, the present disclosure provides a method for promoting melanin production, which includes a step of administering a composition containing fructose 1,6-bisphosphate or a salt, a solvate, a stereoisomer or a hydrate thereof as an active ingredient to a subject in need thereof.

In another aspect, the present disclosure provides fructose 1,6-bisphosphate or a salt, a solvate, a stereoisomer or a hydrate thereof for use in preventing gray hair or promoting black hair.

In another aspect, the present disclosure provides fructose 1,6-bisphosphate or a salt, a solvate, a stereoisomer or a hydrate thereof for use in preventing, improving or treating vitiligo or hypochromatism.

In another aspect, the present disclosure provides fructose 1,6-bisphosphate or a salt, a solvate, a stereoisomer or a hydrate thereof for use in promoting melanin production.

EXAMPLES

Hereinafter, the present disclosure is described in detail through examples. The following examples are provided only as examples for helping the understanding of the present disclosure and the present disclosure is not limited by the examples.

Test Example 1

Evaluation of Melanin Synthesis-Promoting Effect in Normal Human Melanocytes Depending on Concentration of Fructose 1,6-bisphosphate 1. Evaluation Method Normal human epidermal melanocytes (GIBCO™, ThermoFisher Scientific, USA) were treated with fructose 1,6-bisphosphate at 0 (untreated group), 0.1, 1, 10 or 100 ppm and then cultured for 6 days. After the culturing, the cells were lysed with 1 N NaOH and absorbance was measured at 475 nm. Relative melanin production was represented with respective to the absorbance of the untreated group not treated with fructose 1,6-bisphosphate as 100%. A higher absorbance means a higher melanin content. The result is shown in FIG. 1. Also, the e-tube images of the melanocytes lysed with NaOH are shown in FIG. 2.

2. Evaluation Result

From FIG. 1 and FIG. 2, it was confirmed that fructose 1,6-bisphosphate exhibits the effect of promoting melanin production in melanocytes. In particular, the effect was significantly high in the 100 ppm treatment group.

Test Example 2

Evaluation of Effect of Preventing Gray Hair and Promoting Black Hair of Fructose 1,6-Bisphosphate Trisodium Salt in Human Hair Follicle 1. Isolation of Human Hair Follicles Occipital scalp tissue was obtained from a 45-year-old male who received hair follicle transplantation surgery due to hair loss. Hair follicle samples were isolated from the obtained occipital scalp tissue using a microscope. A total of 15 hair follicle samples were prepared for 3 groups, with 5 samples per each group.

2. Culturing of Hair Follicles

The hair follicle samples were cultured on a 24-well plate (Nunc, Wiesbaden, Germany) containing 500 μL of a culture medium, with 5 samples per well. As the culture medium, William's E medium (GIBCO, NY, USA) containing 2 mM L-glutamine (PAA, Coelbe, Germany), 10 μg/mL insulin, 10 ng/mL hydrocortisone (Sigma, St Louis, Mo.), 0.1% Fungizone (GIBCO, NY, USA), 10 μg/mL streptomycin and 100 U/mL penicillin (GIBCO, NY, USA) was used. After simultaneously treating with hydrogen peroxide and a fructose 1,6-bisphosphate trisodium salt (FBP-Na3H) at 1000 μM and 100 ppm, respectively, the samples were cultured for 3 days. For comparison, control groups were treated with 1000 μM hydrogen peroxide ($H_2O_2$) only or with neither hydrogen peroxide nor the fructose 1,6-bisphosphate trisodium salt.

3. Observation of Melanin through Fontana-Masson Staining

After the treatment, the sample was fixed with formalin, washed with water, dehydrated with alcohol and xylene, and then embedded in paraffin according to a common tissue-processing procedure. After preparing 8-μm tissue sections using a microtome (Leica RM 2145, Germany) and staining with Fontana-Masson stain, the hair follicles were imaged using a dissecting microscope (Dongwon CNS, Korea). The obtained images are shown in FIG. 3.

4. Evaluation Result

From FIG. 3, it was confirmed that the fructose 1,6-bisphosphate trisodium salt exhibits the effect of preventing gray hair by promoting melanin production in human hair follicles and preventing decreased melanin production in hair bulbs due to damage caused by hydrogen peroxide, etc.

Hereinafter, formulation examples of the composition according to the present disclosure are described. However, they are merely specific non-limiting examples and may be changed variously.

[Formulation Example 1]

Shampoo

A shampoo was prepared by a common method according to the composition described in Table 1.

TABLE 1

| Ingredients | Contents (wt %) |
|---|---|
| Fructose 1,6-bisphosphate | 5 |
| Ammonium lauryl sulfate (ALS) | 20.0 |
| Ammonium laureth sulfate (ALES) | 20.0 |
| Cocamide MIPA | Adequate |
| Disodium EDTA | 0.03 |
| Carbomer | Adequate |
| Ethanol | Adequate |
| Cocamidopropyl betaine | 6.0 |
| Dimethicone (50%) | 2.0 |
| Dimethicone (70%) | 2.0 |
| DL-panthenol | Adequate |
| Tocopheryl acetate | Adequate |
| Triethanolamine | Adequate |
| Menthol | Adequate |
| Methylchloroisothiazolinone/methylisothiazolinone mixure (MC/IMI) | 0.03 |
| Methylparaben | Adequate |
| Antiseptic, colorant and flavor | Adequate |
| Purified water | Balance |

[Formulation Example 2]

Hair Rinse

A hair rinse was prepared by a common method according to the composition described in Table 2.

TABLE 2

| Ingredients | Contents (wt %) |
|---|---|
| Fructose 1,6-bisphosphate | 5 |
| Propylene glycol | 2.0 |
| Cetyltrimethylammonium chloride | 1.0 |
| Cetyl alcohol | 3.0 |
| Stearyl alcohol | 3.0 |
| Mineral oil | 0.5 |
| Citric acid | 0.2 |
| Polydimethylsiloxane | 1.0 |
| Antiseptic, colorant and flavor | Adequate |
| Purified water | Balance |

[Formulation Example 3]

Softening lotion

A softening lotion was prepared by a common method according to the composition described in Table 3.

TABLE 3

| Ingredients | Contents (wt %) |
|---|---|
| Fructose 1,6-bisphosphate | 5 |
| Glycerin | 3.0 |
| Butylene glycol | 2.0 |
| Propylene glycol | 2.0 |
| Carboxyvinyl polymer | 0.1 |
| ethanol | 10.0 |
| Triethanolamine | 0.1 |
| Antiseptic, colorant and flavor | Adequate |
| Purified water | Balance |

[Formulation Example 4]

Nourishing Lotion

A nourishing lotion was prepared by a common method according to the composition described in Table 4.

TABLE 4

| Ingredients | Contents (wt %) |
|---|---|
| Fructose 1,6-bisphosphate | 5 |
| Beeswax | 4.0 |
| Polysorbate 60 | 1.5 |
| Sorbitan sesquioleate | 0.5 |
| Liquid paraffin | 5.0 |
| Squalane | 5.0 |
| Caprylic/capric triglyceride | 5.0 |
| Glycerin | 3.0 |
| Butylene glycol | 3.0 |
| Propylene glycol | 3.0 |
| Carboxyvinyl polymer | 0.1 |
| Triethanolamine | 0.2 |
| Antiseptic, colorant and flavor | Adequate |
| Purified water | Balance |

[Formulation Example 5]

Nourishing Cream

A nourishing cream was prepared by a common method according to the composition described in Table 5.

TABLE 5

| Ingredients | Contents (wt %) |
|---|---|
| Fructose 1,6-bisphosphate | 5 |
| Beeswax | 10.0 |
| Polysorbate 60 | 1.5 |
| Sorbitan sesquioleate | 0.5 |
| Liquid paraffin | 10.0 |
| Squalane | 5.0 |
| Caprylic/capric triglyceride | 5.0 |
| Glycerin | 5.0 |
| Butylene glycol | 3.0 |
| Propylene glycol | 3.0 |
| Triethanolamine | 0.2 |
| Antiseptic, colorant and flavor | Adequate |
| Purified water | Balance |

[Formulation Example 6]

Massage Cream

A massage cream was prepared by a common method according to the composition described in Table 6.

TABLE 6

| Ingredients | Contents (wt %) |
|---|---|
| Fructose 1,6-bisphosphate | 5 |
| Beeswax | 10.0 |
| Polysorbate 60 | 1.5 |
| Sorbitan sesquioleate | 0.8 |
| Liquid paraffin | 40.0 |
| Squalane | 5.0 |
| Caprylic/capric triglyceride | 4.0 |
| Glycerin | 5.0 |
| Butylene glycol | 3.0 |
| Propylene glycol | 3.0 |
| Triethanolamine | 0.2 |
| Antiseptic, colorant and flavor | Adequate |
| Purified water | Balance |

[Formulation Example 7]

Pack

A pack was prepared by a common method according to the composition described in Table 7.

TABLE 7

| Ingredients | Contents (wt %) |
|---|---|
| Fructose 1,6-bisphosphate | 5 |
| Polyvinyl alcohol | 13.0 |
| Sodium carboxymethyl cellulose | 0.2 |
| Allantoin | 0.1 |
| Ethanol | 5.0 |
| Nonyl phenyl ether | 0.3 |
| Antiseptic, colorant and flavor | Adequate |
| Purified water | Balance |

[Formulation Example 8]

Powder

A powder was prepared by a common method according to the composition described in Table 8.

TABLE 8

| Ingredients | Contents (wt %) |
|---|---|
| Fructose 1,6-bisphosphate | 5 |
| Lactose | 1 |

[Formulation Example 9]

Tablet

A tablet was prepared by a common method according to the composition described in Table 9.

TABLE 9

| Ingredients | Contents (wt %) |
|---|---|
| Fructose 1,6-bisphosphate | 500 |
| Cornstarch | 50 |
| Lactose | 50 |
| Magnesium stearate | 2 |

[Formulation Example 10]

Capsule

A capsule was prepared by a common method according to the composition described in Table 10. After mixing the ingredients, the mixture was filled in a gelatin capsule according to a common capsule preparation method.

TABLE 10

| Ingredients | Contents (wt %) |
|---|---|
| Fructose 1,6-bisphosphate | 600 |
| Cornstarch | 100 |
| Lactose | 100 |
| Magnesium stearate | 2 |

[Formulation Example 11]
Drink

A drink was prepared by a common method according to the composition described in Table 11.

TABLE 11

| Ingredients | Contents (wt %) |
| --- | --- |
| Fructose 1,6-bisphosphate | 0.1 |
| Glucose | 10 |
| Citric acid | 2 |
| Purified water | 100 |

The present disclosure relates to and includes at least the following embodiments.

[Embodiment 1] A composition for preventing gray hair or promoting black hair, which contains fructose 1,6-bisphosphate or a salt, a solvate, a stereoisomer or a hydrate thereof as an active ingredient.

[Embodiment 2] A composition for preventing, improving or treating vitiligo or hypochromatism, which contains fructose 1,6-bisphosphate or a salt, a solvate, a stereoisomer or a hydrate thereof as an active ingredient. [Embodiment 3] A composition for promoting melanin production, which contains fructose 1,6-bisphosphate or a salt, a solvate, a stereoisomer or a hydrate thereof as an active ingredient.

[Embodiment 4] The composition according to any of Embodiments 1 to Embodiment 3, wherein a daily application dosage of the fructose 1,6-bisphosphate or a salt, a solvate, a stereoisomer or a hydrate thereof is more than 10 mg/kg and less than 10,000 mg/kg.

[Embodiment 5] The composition according to any of Embodiments 1 to 4, wherein the fructose 1,6-bisphosphate or a salt, a solvate, a stereoisomer or a hydrate thereof is contained in an amount of 0.06-60 wt % based on the total weight of the composition.

[Embodiment 6] The composition according to any of Embodiments 1 to 5, wherein the composition promotes melanin production in melanocytes.

[Embodiment 7] The composition according to any of Embodiments 1 to 6, wherein the gray hair is caused by aging.

[Embodiment 8] The composition according to any of Embodiments 1 to 7, wherein the composition is a composition for external application to skin. [Embodiment 9] The composition according to any of Embodiments 1 to 8, wherein the composition is a cosmetic composition.

[Embodiment 10] The composition according to any of Embodiments 1 to 9, wherein the composition is a food composition.

[Embodiment 11] The composition according to any of Embodiments 1 to 10, wherein the composition is a pharmaceutical composition.

Although the present disclosure has been described with regard to specific exemplary embodiments, various changes or modifications can be made thereto without departing from the subject matter and scope of the present disclosure. Accordingly, such changes or modifications will be included in the appended claims.

The invention claimed is:

1. A method for preventing gray hair or promoting black hair, comprising administering a composition comprising fructose 1,6-bisphosphate salt, to a human subject for preventing gray hair or promoting black hair,
wherein a daily application dosage of the fructose 1,6-bisphosphate salt is 100 mg/kg.

2. The method according to claim 1, wherein the gray hair is caused by aging.

3. The method according to claim 1, wherein the composition is a composition for external application to skin.

4. The method according to claim 1, wherein the composition is a cosmetic composition, a food composition or a pharmaceutical composition.

5. A method for preventing, improving or treating vitiligo or hypochromatism, comprising administering a composition comprising fructose 1,6-bisphosphate salt, to a human subject for preventing, improving or treating vitiligo, or hypochromatism,
wherein a daily application dosage of the fructose 1,6-bisphosphate salt is 100 mg/kg.

6. The method according to claim 5, wherein the preventing, improving or treating vitiligo or hypochromatism is by promoting the production of melanin in human melanocytes.

7. The method according to claim 5, wherein the composition is a composition for external application to skin.

8. The method according to claim 5, wherein the composition is cosmetic composition, a food composition or a pharmaceutical composition.

9. A method for promoting melanin production in melanocytes, comprising administering a composition comprising fructose 1,6-bisphosphate salt, to a human subject for promoting melanin production in melanocytes,
wherein a daily application dosage of the fructose 1,6-bisphosphate salt is 100 mg/kg.

10. The method according to claim 9, wherein the composition is a composition for external application to skin.

11. The method according to claim 9, wherein the composition is cosmetic composition, a food composition or a pharmaceutical composition.

* * * * *